United States Patent
Ichikawa et al.

(10) Patent No.: US 7,015,264 B2
(45) Date of Patent: Mar. 21, 2006

(54) DEPROTEINIZING AGENT, DEPROTEINIZED NATURAL RUBBER LATEX USING THE SAME, AND METHOD OF PRODUCING RUBBER PRODUCT

(75) Inventors: Naoya Ichikawa, Kobe (JP); Yoshiaki Miyamoto, Kobe (JP); Akihiko Hamada, Kobe (JP)

(73) Assignee: Sumitomo Rubber Industries, Ldt., Kobe (JP)

( * ) Notice: Subject to any disclaimer, the term of this patent is extended or adjusted under 35 U.S.C. 154(b) by 0 days.

(21) Appl. No.: 10/615,839

(22) Filed: Jul. 10, 2003

(65) Prior Publication Data

US 2004/0014876 A1    Jan. 22, 2004

Related U.S. Application Data

(62) Division of application No. 09/842,903, filed on Apr. 27, 2001, now abandoned.

(30) Foreign Application Priority Data

| Apr. 28, 2000 | (JP) | ............................. 2000-130543 |
| May 12, 2000 | (JP) | ............................. 2000-140535 |
| Aug. 18, 2000 | (JP) | ............................. 2000-248902 |

(51) Int. Cl.
  *C08C 1/04*    (2006.01)
  *C12N 9/96*    (2006.01)

(52) U.S. Cl. ........................ 524/17; 524/78; 524/332.5; 524/333.1

(58) Field of Classification Search ................ 524/17, 524/78, 332.5; 525/333.1
See application file for complete search history.

(56) References Cited

U.S. PATENT DOCUMENTS

| 4,508,825 A | | 4/1985 | Kim et al. |
| 5,585,459 A | * | 12/1996 | Tanaka et al. ............. 528/486 |
| 5,910,567 A | * | 6/1999 | Tanaka et al. ............. 528/491 |
| 5,998,512 A | | 12/1999 | Schloman |

FOREIGN PATENT DOCUMENTS

| EP | 584597 A1 | * | 3/1994 |
| EP | 0 624 601 A1 | | 11/1994 |
| EP | 0 630 907 A1 | | 12/1994 |
| EP | 0 816 417 A1 | | 1/1998 |
| JP | 656902 A | | 3/1994 |
| JP | 10279607 A | * | 10/1998 |
| JP | 2000-17002 A | | 1/2000 |
| WO | WO 94/25580 A1 | | 11/1994 |
| WO | WO 9628500 A1 | * | 9/1996 |

* cited by examiner

*Primary Examiner*—Kelechi C. Egwim
(74) *Attorney, Agent, or Firm*—Birch, Stewart, Kolasch & Birch, LLP

(57) ABSTRACT

The present invention relates to (1) a deproteinizing agent for natural rubber latex, comprising a protease and one or more water-soluble polymers as an active component; (2) a deproteinized natural rubber latex, which is prepared by subjecting to a deproteinization treatment using the deproteinizing agent, and a method of producing the same; (3) a method of producing a rubber product, which comprises incorporating at least a vulcanizing agent into the latex (2), dipping a mold in the resulting compound latex, and vulcanizing and drying a rubber film formed on the mold; and (4) a method of producing a rubber product, which comprises incorporating at least a heat sensitizer and a vulcanizing agent into the latex (2), dipping a mold in the resulting heat-sensitive coagulable compound latex, and vulcanizing and drying a rubber film formed on the mold.

5 Claims, No Drawings

DEPROTEINIZING AGENT, DEPROTEINIZED NATURAL RUBBER LATEX USING THE SAME, AND METHOD OF PRODUCING RUBBER PRODUCT

This application is a divisional of Ser. No. 09/842,903, filed Apr. 27, 2001, now abandoned.

BACKGROUND OF THE INVENTION

The present invention relates to a deproteinizing agent for removing a protein in a natural rubber, a deproteinized natural rubber latex obtained by using the same, and a method of producing a rubber product using the rubber latex.

Natural rubbers have widely been used in various fields, for example, industrial goods such as automobile tire, belt and adhesive, household goods such as glove, medical appliances such as catheter, lactation appliances, contraceptive device and the like because of features such as large extension, high elasticity and strong film strength.

Among these, glove, medical appliances and lactation appliances are products obtained by dipping a mold for these rubber products in a natural rubber latex and these dipped products are produced by using (a) a so-called direct method of directly dipping a mold in a natural rubber latex, (b) a so-called anode coagulation method of coating a mold with an anode coagulant and dipping the mold in a natural rubber latex, and (c) a so-called heat sensitizing method of dipping a previously heated mold in a natural rubber latex containing a heat sensitizer, thereby gradually depositing a gel on the surface of the mold.

These preparation methods are appropriately selected according to the kind of dipped products. The direct method is employed when producing products such as condom made of a rubber film having a very small thickness, the anode coagulation method is employed when producing a household glove made of a rubber film having a thickness of about 1 mm, and the heat sensitizing method is employed when producing more thick products such as work glove.

By the way, it has recently been reported that, when using medical appliances made of the natural rubber, such as surgical glove and various catheters, immediate (I type) allergy, which shows symptoms such as respiratory distress and anaphylactoid symptom (e.g. vascular edema, urttication, collapse, cyanosis, etc.) within several hours, is caused. It is presumed that such immediate allergy is caused by a protein, as an antigen, in the natural rubber.

Also it has been known that the protein contained in the natural rubber causes variations in quality and vulcanization properties of the natural rubber because the kind and quantity of the protein vary depending on the locality and production season of the natural rubber latex. In addition, the protein can cause deterioration of mechanical characteristics such as creep characteristics and aging resistance and electrical characteristics such as insulating properties.

Accordingly, it has been considered to be important to highly remove a protein from a natural rubber latex and to obtain a so-called deproteinized natural rubber latex wherein the protein is highly removed.

Japanese Published Unexamined Patent (Kokai Tokkyo Koho Hei) No. 6-56902 discloses a method of adding a proteolytic enzyme (protease) and a surfactant to a natural rubber latex, thereby decomposing a protein, and separating a creamy deproteinized natural rubber component by centrifugation.

According to this method, the protein in the natural rubber latex can be removed in a very high level and the nitrogen content (N %) is reduced to 0.1% by weight or less as measured by the Kjeldahl method.

However, a large amount of a surfactant is incorporated into the deproteinized natural rubber latex obtained by the method described above in order to prevent destabilization of the latex due to removal of the protein and to prevent coagulation of rubber particles. Therefore, the dispersion state of rubber particles in the latex is excessively stable.

Therefore, the direct method of directly dipping the mold in the natural rubber latex to form a film causes liquid dripping, thereby making it difficult to form a uniform thin film. Namely, it is difficult to produce a dipped product having a very small film thickness, such as condom, in a uniform film thickness by using the deproteinized natural rubber latex.

The deproteinized natural rubber latex obtained by the method described above has a problem that coagulation of rubber particles can not be effected by a conventional heat sensitizer, thereby making it impossible to form a film according to the formulation of a conventionally used heat sensitizing method.

There is also a problem that a surfactant present in the latex exerts an adverse influence on various physical properties of the rubber product, such as deterioration of the water resistance of the resulting rubber product.

However, the method described in the publication described above has a problem that, since the both of the heat sensitizer and anode coagulant are incorporated into the latex, the latex becomes unstable as compared with a conventional heat sensitizing method using a natural rubber latex, thereby making it impossible to obtain long-term stability and making it hard to control heat-sensitive properties.

The present applicants have previously filed a patent application with respect to such an invention that a dip product having a sufficient film thickness is obtained by using a specific heat sensitizer and a specific anode coagulant in a specific combination and incorporating the specific combination into a deproteinized natural rubber latex wherein rubber particles are excessively stabilized, obtained by the method described above, in a large amount as compared with a conventional formulation (Japanese Published Unexamined Patent (Kokai Tokkyo Koho) No. 2000-17002).

The present applicants have continuously studied to solve such a problem that, since the both of the heat sensitizer and anode coagulant are incorporated into the latex in the method described in the publication described above, the latex becomes unstable as compared with a conventional heat sensitizing method using a natural rubber latex, thereby making it impossible to obtain long-term stability and making it hard to control heat-sensitive properties.

Thus, an object of the present invention is to provide a deproteinizing agent which can realize high deproteinization of a natural rubber latex and provide the latex with sufficient heat-sensitive coagulation properties while maintaining the stability of the deproteinized natural rubber latex for a long term, and to provide a method of preparing a deproteinized natural rubber latex which simultaneously satisfy the stability and heat-sensitive coagulation properties of the latex.

Another object of the present invention is to provide a method capable of producing a uniform dipped product having a very small film thickness from a highly deproteinized natural rubber latex, as a raw material, without causing liquid dripping.

A still another object of the present invention is to provide a method capable of producing a dipped product having a sufficient film thickness from a highly deproteinized natural rubber latex, as a raw material, even in case of the same formulation as that of a conventional heat-sensitive latex using a natural rubber latex, the method capable of easily controlling the heat-sensitive properties.

SUMMARY OF THE INVENTION

The present inventors have intensively studied to solve the problems described above and found such a novel finding that, when a deproteinization treatment is conducted by incorporating a predetermined water-soluble polymer, together with a protease used conventionally in a deproteinization treatment of a natural rubber latex, there can be obtained a natural rubber latex deproteinized highly by the treatment and such a latex shows sufficient heat-sensitive coagulation properties while maintaining the long-term stability. Thus, the present invention has been completed.

That is, the deproteinizing agent for natural rubber latex according to the present invention is characterized in that it comprises a protease and one or more water-soluble polymers as an active component.

According to the deproteinizing agent of the present invention, regardless of its simple constitution as described above, it is made possible to highly deproteinize a protein in a natural rubber latex, to maintain the stability of the deproteinized natural rubber latex for a long term, and to provide the deproteinized natural rubber latex with sufficient heat-sensitive coagulation properties.

The water-soluble polymer in the deproteinizing agent of the present invention is a polymer having at least one hydrophilic functional group selected from a hydroxyl group, a carboxyl group, an amide group and an ester bond, or a salt thereof, a principal chain of the polymer having 100 to 5,000,000 carbon atoms.

Use the polymer described above as the water-soluble polymer makes it possible to simultaneously provide the deproteinized natural rubber latex with the long-term stability and sufficient heat-sensitive coagulation properties. The polymers may be used alone or in combination.

In the present invention, a weight ratio of the-protease to the water-soluble polymer is preferably within a range from 1:1 to 1:200.

The deproteinized natural rubber latex of the present invention is characterized in that it is prepared by subjecting to a deprotenization treatment using the deproteinizing agent of the present invention.

The method of producing a deproteinized natural rubber latex according to the present invention is characterized in that it comprises adding the deproteinizing agent of the present invention to a natural rubber latex, thereby maturing the natural rubber latex, and washing rubber particles in the latex.

The deproteinized natural rubber latex obtained by the method of the present invention is a stable latex, a protein of which is highly removed. Because of its sufficient heat sensitivity, the latex is suited for use as a raw material for producing thick rubber products such as work glove, catheter and the like.

In the method of producing a deproteinized natural rubber latex of the present invention, the amount of the deproteinizing agent is preferably within a range from 0.001 to 10 parts by weight based on 100 parts by weight of the rubber solid content in the natural rubber latex.

The present inventors have studied about the method of producing the rubber product using the natural rubber latex deproteinized by the deproteinizing agent described above and succeeded in obtaining rubber products having good quality, industrially advantageously, by the following methods (1) and (2).

(1) A dipped product made of a film, which has a very small thickness and uniform, can be produced by incorporating a conventionally known vulcanizing agent into the deproteinized natural rubber latex in accordance with the same formulation as in case of a normal compound latex, using the direct (dipping) method.

(2) A dipped product made of a film having a sufficient thickness can be produced by incorporating a conventionally known vulcanizing agent into the deproteinized natural rubber latex in accordance with the same formulation as in case of a normal heat-sensitive compound latex, using the heat sensitizing method.

The method (1) of producing a rubber product using a deproteinized natural rubber latex according to the present invention is characterized in that it comprises adding a protease and one or more water-soluble polymers to a natural rubber latex, thereby subjecting the natural rubber latex to a deproteinization treatment, incorporating at least a vulcanizing agent into the latex, dipping a mold in the resulting compound latex, and vulcanizing and drying a rubber film formed on the mold.

The method (2) of producing a rubber product using a deproteinized natural rubber latex according to the present invention is characterized in that it comprises adding a protease and one or more water-soluble polymers to a natural rubber latex, thereby subjecting the natural rubber latex to a deproteinization treatment, incorporating at least a heat sensitizer and a vulcanizing agent into the latex, dipping a mold in the resulting heat-sensitive coagulating compound latex, and vulcanizing and drying a rubber film formed on the mold.

As described above, since a conventional highly deproteinized natural rubber latex is excessively stabilized by a surfactant, it was difficult to produce a rubber film by the heat sensitizing method. To the contrary, according to the method of producing the rubber product of the present invention since stabilization of the highly deproteinized natural rubber latex is realized by the water-soluble polymer, the stability during storage is sufficient secured, but excess stabilization does not arise.

Therefore, according to the method (1), the protein can be highly removed from the natural rubber latex and, moreover, the dipped product made of a film, which has a very small thickness and uniform, can be produced easily by the direct (dipping) method regardless of use of the highly deproteinized natural rubber latex as the raw material.

According to the method (2), the protein can be highly removed from the natural rubber latex and, moreover, the dipped product made of a thick film can be produced easily by the heat sensitizing method regardless of use of the highly deproteinized natural rubber latex as the raw material.

The deproteinized natural rubber product thus produced shows not only low allergy because of removal of the protein, but also excellent characteristics with respect to softness and extension. Furthermore, a thin and uniform rubber film can be produced by the direct dipping method and a comparatively thick rubber product can be produced by the heat sensitizing method.

The heat sensitizer used in the method (2) is preferably a water-soluble polymer type heat sensitizer.

The amount of the heat sensitizer is preferably adjusted within a range from 0.1 to 10 parts by weight based on 100 parts by weight of the rubber solid content in the deproteinized latex.

DETAILED DESCRIPTION OF THE INVENTION

The present invention will be described in detail below.

[Deproteinizing Agent]

The deproteinizing agent of the present invention contains a protease and one or more water-soluble polymers as an active component, as described above.

Protease

The protease used in the deproteinizing agent of the present invention is not specifically limited and a conventionally known one can be used and, for example, an alkaline protease is preferable. The protease may be derived from any of bacteria, filamentous bacteria and yeast, and the protease is preferably derived from bacteria, particularly preferably from the genus *Bacillus*. It is also possible to use enzymes such as lipase, esterase, amylase, lacase and cellulase in combination.

Among these, protease KAP having a resistance to the surfactant manufactured by Kao Corp. is used particularly preferably.

When using the alkaline protease, its activity [measured value obtained by modification of the Anson-hemoglobin method (Anson. M. L. J. Gen. Physiol., 22, 79 (1938))] is within a range from 0.1 to 50 APU/g, and preferably within a range from 1 to 25 APU/g.

The amount of the protease varies depending on the amount of the deproteinizing agent described below of the present invention and the activity of the protease itself, and is not specifically limited. In general, the amount of the deproteinizing agent is adjusted so that the amount of the protease in the deproteinizing agent is preferably adjusted within a range from 0.0001 to 20 parts by weight, and more preferably within a range from 0.001 to 10 parts by weight, based on 100 parts by weight of the rubber component in the natural rubber latex. When the amount of the protease is within the range described above, a protein in the latex can be sufficiently decomposed while maintaining the activity of the protease. Alternatively, the effect corresponding to the amount of the protease can be exerted effectively and, therefore, it is advantageous in view of the cost.

Water-soluble Polymer

Examples of the water-soluble polymer which can be used in the deproteinizing agent include a polymer having at least one hydrophilic functional group selected from a hydroxyl group, a carboxyl group, an amide group and an ester bond, or a salt thereof, a principal chain of the polymer having 100 to 5,000,000 carbon atoms.

More specific examples are those, wherein the principal chain has 100 to 5,000,000 carbon atoms, among (meth)acrylate polymer, alginate polymer, vinyl polymer, polyethylene oxide polymer and cellulose polymer.

Examples of the (meth)acrylate polymer include sodium polyacrylate, sodium polymethacrylate, ammonium polyacrylate, and ammonium polymethacrylate.

Examples of the alginate polymer include sodium alginate, ammonium alginate, potassium alginate, and propylene glycol alginate.

Examples of the vinyl polymer include polyvinyl alcohol (PVA), and a potassium salt (saponified substance) of PVA.

Examples of the polyethylene oxide polymer include polyethylene oxide and polypropylene oxide.

Examples of the cellulose polymer include carboxymethylcellulose (CMC), hydroxyethylcellulose, hydroxypropylcellulose, and cellulose xanthogenate.

The water-soluble polymer in the deproteinizing agent of the present invention is not limited to the polymers described above and there can be used protein-based water-soluble polymer (e.g. casein, etc.), sodium carboxymethyl-starch, sodium starch phosphate or the like.

A small amount of a surfactant can also be added to the deproteinizing agent of the present invention, together with the polymer described above. When the content of the surfactant is large, the stability of the latex is excessive and the effect of the present invention is likely to be impaired. Accordingly, a sufficient consideration must be paid to the amount.

As the stabilizer used in the deproteinization treatment to a conventional natural rubber latex, "polyoxyethylene nonionic surfactant" is known. However, since a hydrophobic group of such a surfactant is merely that obtained by bonding about several to thirty ethylene glycols, the polyoxyethylene nonionic surfactant is not included in the category of the water-soluble polymer in the present invention.

The amount of the water-soluble polymer varies depending on the amount of the deproteinizing agent described below of the present invention and properties of the water-soluble polymer itself and is not specifically limited. However, the amount of the deproteinizing agent is generally adjusted so that the content of the water-soluble polymer is preferably within a range from 0.1 to 10 parts by weight, and more preferably within a range from 0.5 to 3 parts by weight, based on 100 parts by weight of the rubber content in the natural rubber latex. When the content of the water-soluble polymer is within the range described above, it is made possible to simultaneously satisfy the stability and heat-sensitive coagulation properties of the deproteinized natural rubber latex.

Ratio of Protease to Water-soluble Polymer

The protease and water-soluble polymer in the deproteinizing agent of the present invention are contained in a weight ratio within a range from 1:1 to 1:200, as described above.

When the proportion of the protease is smaller than the above range or the proportion of the water-soluble polymer exceeds the above range, there is a fear that a sufficient deproteinizing effect can not be obtained and the heat-sensitive coagulation properties of the latex are impaired.

On the other hand, when the protease is contained in the proportion which exceeds the above range, an influence is hardly exerted on the deproteinizing effect and disadvantages such as high cost are likely to arise. When the proportion of the water-soluble polymer is smaller than the above range, the stability of the latex is likely to be impaired.

The ratio of the protease to the water-soluble polymer in the deproteinizing agent of the present invention is preferably within a range from 1:5 to 1:100, and more preferably within a range from 1:10 to 1:50, among the above range.

[Deproteinized Natural Rubber Latex and Method of Producing the Same]

The deproteinized natural rubber latex of the present invention is characterized in that it is prepared by subjecting to a deprotenization treatment using the deproteinizing agent of the present invention.

The method of producing a deproteinized natural rubber latex according to the present invention is characterized in that it comprises adding the deproteinizing agent of the present invention to a natural rubber latex, thereby maturing the natural rubber latex, and cleaning rubber particles in the latex.

Natural Rubber Latex

The natural rubber latex used to prepare the deproteinized natural rubber obtained from a rubber sap and a concentrated latex stored in ammonia.

Amount of Deproteinizing Agent

In case of subjecting the natural rubber latex to the deproteinization treatment, the amount of the deproteinizing agent is decided by the content of the protease in the deproteinizing agent and the activity of the protease, and is usually set within a range from 0.0001 to 10 parts by weight, and preferably within a range from 0.001 to 10 parts by weight, based on 100 parts by weight of the rubber content in the latex.

When the amount of the deproteinizing agent is smaller than the above range, the deproteinizing effect becomes poor and it is likely to become impossible to sufficiently remove a fear of the occurrence of immediate allergy caused by the protein.

On the other hand, even if the deproteinizing agent is incorporated in the amount that exceeds the above range, the expected effect can not be exerted or it is likely to become impossible to obtain the effect corresponding to the cost.

Deproteinization Treatment

The deproteinization treatment is conducted by adding a deproteinizing agent of the present invention to a natural rubber latex as the raw material, as described above, and maturing the latex for about several tens minutes to one week, more preferably about 1 to 3 days. A protein in the natural rubber latex can be decomposed.

This maturing treatment may be conducted while stirring the latex or allowing it to stand. If necessary, the temperature may be controlled and is controlled within a range from 5 to 90° C., and preferably from 20 to 60° C. to obtain sufficient activity of the enzyme. When the temperature is lower than 5° C., there is a fear that the enzyme reaction does not proceed. On the other hand, when the temperature exceeds 90° C., there is a fear that the enzyme is devitalized.

The cleaning (purification) treatment of rubber particles in the latex after the deproteinization treatment includes, but is not specifically limited to, a treatment of concentrating the latex by centrifugation or ultra filtration and separating the non-rubber component transferred in water such as protein decomposition product and the rubber particles in the latex, or a treatment of separating the rubber particles by cohesion using an acid.

In case the cleaning (purification) treatment after the deproteinization treatment is conducted by a centrifugation treatment, a sufficient deproteinizing effect can be obtained by dispersing a cream component separated in the upper layer by centrifugation under the conditions of 5,000 to 15,000 rpm for about 1 to 60 minutes (or gravity acceleration of about 10000 G for 1 to 60 minutes) again in water having almost the same volume as that of the cream component. The stability and heat-sensitive coagulation properties of the latex can be sufficiently maintained by the water-soluble polymer which is previously added before the deproteinization treatment and remained even after the purification treatment.

Degree of Deproteinization

The degree of the deproteinization attained in the present invention is adjusted so that the nitrogen content (N %) as determined by the Kjeldahl method is 0.1% or less, preferably 0.05% or less, and more preferably 0.02% or less.

When the nitrogen content exceeds the above range, there is a fear that the occurrence of the allergic reaction can not be sufficiently suppressed because of insufficient degree of the deproteinization.

The degree of the deproteinization can also be confirmed by the presence or absence of adsorption and degree of adsorption on the basis of the protein by means of an infrared absorption spectrum. In the rubber treated by using the deproteinizing agent of the present invention, an absorption at 3320 $cm^{-1}$ derived from short-chain peptide or amino acid may be observed. However, it is preferable that an absorption at 3280 $cm^{-1}$ derived from polymer peptide as a cause for allergy is small. It is more preferable that any absorption at 3280 $cm^{-1}$ is not observed.

[Method of Producing Rubber Product]

As described above, the method of producing a rubber product according to the present invention is characterized in that:

(1) it comprises adding a protease and one or more water-soluble polymers to a natural rubber latex, thereby subjecting the natural rubber latex to a deproteinization treatment, incorporating at least a vulcanizing agent into the latex, dipping a mold in the resulting compound latex, and vulcanizing and drying a rubber film formed on the mold, or (2) it comprises adding a protease and one or more water-soluble polymers to a natural rubber latex, thereby subjecting the natural rubber latex to a deproteinization treatment, incorporating at least a heat sensitizer and a vulcanizing agent into the latex, dipping a mold in the resulting heat-sensitive coagulating compound latex, and vulcanizing and drying a rubber film formed on the mold.

[Production of Thin Film Dipped Product by Direct Method]

Preparation of Compound Latex

The compound latex used to produce the dipped product by the direct method is obtained by incorporating at least a vulcanizing agent into a natural rubber latex deproteinized by the method described above. This compound latex is used as the raw material in the production of dipped products made of a thin film, such as surgical glove and condom.

Vulcanizing Agent

Examples of the vulcanizing agent include sulfur and organic sulfur-containing compound. The amount of the vulcanizing agent is not specifically limited, but is usually set within a range from 0.5 to 3 parts by weight based on 100 parts by weight of the rubber solid content of the latex.

In the preparation of the compound latex, conventionally known various vulcanization compounding agents such as vulcanization accelerators auxiliary vulcanization accelerators and vulcanization retardants can also be incorporated, in addition to the vulcanizing agents described above.

Examples of the vulcanization accelerator include PX (zinc N-ethyl-N-phenyldithiocarbamate), PZ (zinc dimethyldithiocarbamate), EZ (zinc diethyldithiocarbamate), BZ (zinc dibutyldithiocarbamate) and MZ (zinc salt of 2-mercaptobenzothiazole). These vulcanization accelerators can be used alone or in combination. The amount of the vulcanization accelerator is preferably within a range from about 0.5 to 3 parts by weight based on 100 parts by weight of the rubber solid content of the latex.

Examples of the auxiliary vulcanization accelerator include zinc white. The amount of the auxiliary vulcanization accelerator is preferably within a range from about 0.5 to 3 parts by weight based on 100 parts by weight of the rubber solid content of the latex.

Other Additives

According to properties requited to the rubber product, other compounding agents other than vulcanization compounding agents can be added to the compound latex.

Examples of the other additive include conventionally known various additives such as antioxidants, fillers, plasticizers, softeners and reinforcers.

As the antioxidant, non-contaminating phenols such as CPL (hindered phenol) and antage W-300 [4,4'-butylidenbis-(3-methyl-6-t-butylphenol) are preferred, but amines such as octylated diphenylamine may also be used. The amount of the antioxidant is preferably within a range from about 0.5 to 3 parts by weight based on 100 parts by weight of the rubber solid content of the latex.

Examples of the filler include kaolin clay, hard clay and calcium carbonate. The amount of the filler is preferably 10 parts by weight or less based on 100 parts by weight of the rubber solid content of the latex.

A dispersant may be incorporated to improve dispersion of various additives described above into the rubber latex. Examples of the dispersant include various surfactants, particularly anionic surfactant. The amount of the dispersant is preferably within a range from about 0.3 to 1.0 parts by weight based the weight of the components to be dispersed. When the content of the surfactant increases, the stability of the latex becomes excessive and the effect of simultaneously satisfying the stability and heat-sensitive coagulation properties of the present invention is likely to be impaired and the process ability is likely to be impaired by an increase in viscosity. Accordingly, in case of incorporating a surfactant as the dispersant, an attention must be paid to the amount must.

Production of Thin Film Dipped Product

A mold used in the production of the thin film dipped product by the direct method, i.e. the above method (1), is not specifically limited and conventionally known various molds such as ceramic mold and grass mold can be used.

The preheating temperature of the mold and the dipping time of the mold in the latex are set according to the composition of the compound latex such as kind and amount of the vulcanization compounding agent, and the thickness required to the rubber film, and is not specifically limited. In case a rubber glove having a thickness ranging from about 0.01 to 0.1 mm is produced by the method of the present invention, a mold heated previously to a temperature within a range from 30 to 100° C., preferably from 50 to 70° C., is dipped in a latex for 3 to 60 seconds, preferably about 5 to 20 seconds.

The conditions for vulcanizing the rubber film formed on the surface of the mold are set according to the kind and amount of the vulcanization compounding agent, and the thickness of the rubber film formed on the surface of the mold, and is not specifically limited. In case a rubber glove having a thickness ranging from about 0.01 to 0.1 mm is produced by the method of the present invention, vulcanization may be usually conducted at a temperature within a range from 80 to 120° C., preferably from 90 to 110° C., for 10 to 40 minutes, preferably 20 to 30 minutes.

Also the drying of the rubber film is not specifically limited, and may be conducted in the same manner as in conventional procedure of drying the rubber film formed by the direct (dipping) method.

[Production of Thick Film Dipped Product by Heat Sensitizing Method]

Preparation of Heat-sensitive Coagulable Compound Latex

The heat-sensitive coagulable compound latex used to produce the dipped product by the heat sensitizing method is obtained by incorporating at least a vulcanizing agent and a heat sensitizer into a natural rubber latex deproteinized by the method described above. This heat-sensitive coagulable compound latex is used as the raw material in the production of dipped products made of a thick film, such as work glove and catheter.

Heat Sensitizer

Examples of the heat sensitizer include conventionally known various heat sensitizers such as inorganic and organic ammonium salt, and water-soluble polymer type heat sensitizer. Among these, a water-soluble polymer type heat sensitizer is preferably used in view of maintaining the stability of the deproteinized natural rubber latex.

Examples of the inorganic and organic ammonium salt include ammonium nitrate, ammonium acetate, and various zinc ammonium complexes.

Specific examples of the water-soluble polymer type heat sensitizer include polyvinyl methyl ether (PVME), polyalkylene glycol, polyether polyformal, and functional polysiloxane. Among these, a heat sensitizer having a cloud point of not less than normal temperature and not more than 100° C. is more preferred.

The amount of the heat sensitizer is not specifically limited, but the heat sensitizer is preferably incorporated in the amount within a range from 0.1 to 10 parts by weight based on 100 parts by weight of the rubber solid content in the deproteinized natural rubber latex to improve the film forming properties.

When the amount is smaller than the above range, it is advantageous to form a very thin rubber film, however, liquid dripping arises in case of dipping the mold in the latex and a variation of thickness of the formed rubber film is likely to arise. On the other hand, when the amount of the heat sensitizer exceeds the above range, it is advantageous to form a very thin rubber film, however, liquid dripping arises in case of dipping the mold in the latex and a variation of thickness of the formed rubber film is likely to arise.

The amount of the heat sensitizer is particularly preferably within a range from 0.5 to 5 parts by weight.

Vulcanizing Agent

Examples of the vulcanizing agent used to prepare the heat-sensitive coagulable latex include the same vulcanizing agent as those used in the preparation of "compound latex. The amount of the vulcanizing agent is not specifically limited similar to the above "compound latex", but is usually set within a range from 0.5 to 3 parts by weight based on 100 parts by weight of the rubber solid content of the latex.

Conventionally known various vulcanization compounding agents such as vulcanization accelerators, auxiliary vulcanization accelerators and vulcanization retardants can also be incorporated into the heat-sensitive coagulable compound latex, in addition to the heat sensitizers and vulcanizing agents described above. Examples of the vulcanization accelerator and auxiliary vulcanization accelerator may be the same as those used in preparation of the above "compound latex".

Other Additives

According to properties requited to the rubber product, other compounding agents other than vulcanization compounding agents can be added to the heat-sensitive coagulable compound latex. Examples of the other additive include the same additives as those used in the preparation of the above "compound latex".

Production of Thick Film Dipped Product

A mold used in the production of the thick film dipped product by the direct method, i.e. the above method (2), is not specifically limited and conventionally known various molds such as ceramic mold and grass mold can be used.

In the production of the thick film dipped product by the heat sensitizing method of the present invention, it is preferred to previously incorporate a coagulant such as heat sensitizer into the latex, and to previously heat a mold to be dipped in the latex.

The preheating temperature of the mold and the dipping time of the mold in the latex are set according to the composition of the heat-sensitive coagulable compound latex such as kind and amount of the heat sensitizer and vulcanization compounding agent, and the thickness required to the rubber film, and is not specifically limited. In case a rubber glove having a thickness ranging from about 1 to 3 mm is produced by the method of the present invention, a mold heated previously to a temperature within a range from 70 to 140° C., preferably from 90 to 110° C., is dipped in a latex for 1 to 60 seconds, preferably about 10 to 30 seconds.

The conditions for vulcanizing the rubber film formed on the surface of the mold are set according to the kind and amount of the vulcanization compounding agent, and the thickness of the rubber film formed on the surface of the mold, and is not specifically limited. In case a rubber glove having a thickness ranging from about 1 to 3 mm is produced by the method of the present invention, vulcanization may be usually conducted at a temperature within a range from 80 to 120° C., preferably from 90 to 110° C., for 30 to 90 minutes, preferably 50 to 70 minutes.

Also the drying of the rubber film is not specifically limited, and may be conducted in the same manner as in conventional procedure of drying the rubber film formed by the heat sensitizing method.

EXAMPLES

The following Examples and Comparative Examples further illustrate the present invention.

Example 1

(1) Preparation of Deproteinizing Agent

An alkaline protease and ammonium polyacrylate as the water-soluble polymer were mixed in a weight ratio of 2:98 to obtain a deproteinizing agent.

(2) Preparation of Deproteinized Natural Rubber Latex

After a high ammonia latex of a natural rubber was diluted so that the rubber solid content of becomes 30% by weight, the deproteinizing agent described above was added and the mixture was allowed to stand at 30° C. for 24 hours.

After standing, the latex was subjected to a centrifugation treatment at 13,000 rpm for 30 minutes and the cream component separated in the upper layer was taken out and then dispersed again in water having the same volume as that of the cream component to obtain a deproteinized natural rubber latex.

(3) Preparation of Compound Latex Having Heat Sensitivity

Based on 100 parts by weight of the rubber solid content in the deproteinized natural rubber latex, 1 part by weight of colloidal sulfur (vulcanizing agent) dispersed in water, 1 part by weight of zinc white (auxiliary vulcanization accelerator), 1 part by weight of a vulcanization accelerator BZ (zinc dibutyldithiocarbamate, "NOCCELAR BZ" manufactured by OUCHISHINKO CHEMICAL INDUSTRIAL CO., LTD.) and 0.3 parts by weight of a nonionic surfactant ("EMULVIN" manufactured by BASF Corp.) were added, followed by maturing at 40° C. for 24 hours.

After maturing, the compound latex was cooled to 25° C. and the pH was adjusted to 8.5.using 10% formalin. Then, polyvinyl methyl ether as the heat sensitizer was added in the amount of 0.5 parts by weight based on 100 parts by weight of the rubber solid content in the latex.

(4) Production of Rubber Product

A ceramic test tube (having a diameter of 5 cm) preheated to 90° C. was dipped in the resulting compound latex for heat-sensitive molding for 30 seconds and then vulcanized at 100° C. for 90 minutes to obtain a rubber film.

Examples 2 to 5

As the deproteinizing agent, a mixture of an alkaline protease and sodium alginate(Example 2)or sodium polyacrylate (Example 3), carboxymethylcellulose (Example 4) or ammonium polyacrylate (Example 5) as the water-soluble polymer in a weight ratio of 2:98 was used.

In the same manner as in "preparation of deproteinized rubber latex" and "compound latex having heat sensitivity" of Example 1, except that those described above were used as the deproteinizing agent, compound latexes for heat-sensitive molding were obtained.

In the same manner as in "production of rubber product" of Example 1, except that the compound latex for heat-sensitive molding was used, rubber films were produced.

With respect to Example 5, after the redispersion treatment in "preparation of deproteinized natural rubber latex", the centrifugation treatment and redispersion treatment were conducted again under the same treatment conditions (that is, the centrifugation treatments were conducted twice).

Comparative Examples 1 to 3

As the deproteinizing agent, a mixture (Comparative Example 1)of an alkaline protease and polyoxyethylene oleyl ether (POE oleyl ether) as the nonionic surfactant in a weight ratio of 2:98, a mixture (Comparative Example 2) of an alkaline protease and polyoxyethylene sorbitan monooleate (POE sorbitan monooleate) as the nonionic surfactant in a weight ratio of 2:98, or a mixture of an alkaline protease and polyoxyethylene nonyl phenyl ether (POE nonyl phenyl ether) as the nonionic surfactant in a weight ratio of 2:98 was used.

In the same manner as in "preparation of deproteinized rubber latex" and "compound latex having heat sensitivity" of Example 1, except that those described above were used as the deproteinizing agent, compound latexes for heat-sensitive molding were obtained.

In the same manner as in "production of rubber product" of Example 1, except that the compound latex for heat-sensitive molding was used, rubber films were produced.

A nonionic surfactant was incorporated into the compound latex for heat-sensitive molding in Comparative Examples 1 to 3 in the total amount of 1.28 parts by weight based on 100 parts by weight of the rubber solid content.

Control (Blank Test)

A high ammonia latex of a natural rubber was diluted so that the rubber solid content of becomes 30% by weight and then subjected to a centrifugation treatment at 13,000 rpm for 30 minutes. The cream component separated in the upper layer was taken out and then dispersed again in water having the same volume as that of the cream component to obtain a deproteinized natural rubber latex.

Based on 100 parts by weight of the rubber solid content in the deproteinized natural rubber latex, 1 part by weight of colloidal sulfur (vulcanizing agent) dispersed in water, 1 part by weight of zinc white (auxiliary vulcanization accelerator), 1 part by weight of a vulcanization accelerator BZ (zinc dibutyldithiocarbamate, "NOCCELAR BZ" manufactured by OUCHISHINKO CHEMICAL INDUSTRIAL CO., LTD.) and 0.3 parts by weight of a nonionic surfactant ("EMULVIN" manufactured by BASF Corp.) were added, followed by maturing at 40° C. for 24 hours., After maturing, the compound latex was cooled to 25° C. and the pH was adjusted to 8.5 using 10% formalin. Then, polyvinyl methyl ether as the heat sensitizer was added in the amount of 0.5 parts by weight based on 100 parts by weight of the rubber solid content in the latex.

Production of Rubber Film

A ceramic test tube (having a diameter of 5 cm) preheated to 90° C. was dipped in the resulting compound latex for heat-sensitive molding for 30 seconds and then vulcanized at 100° C. for 90 minutes to obtain a rubber film.

With respect to Examples 1 to 5, Comparative Examples 1 to 3 and control, the active component and ratio of the used deproteinization treatment, the amount of the deproteinizing agent, the amount of the surfactant, and the number of centrifugation treatment are shown in Table 1.

In Table 1, "ratio" in the column of "deproteinizing agent" is "ratio" (% by weight) of the components listed in the column of "active component". "Amount" in the same column is an amount (parts by weight) of the deproteinizing agent based on 100 parts by weight of the rubber solid content of the latex. "Amount" in the column of "surfactant" is an amount (parts by weight) of the nonionic surfactant based on 100 parts by weight of the rubber solid content of the latex before the addition of the heat sensitizer. In "amount" of the column of "surfactant" in Comparative Examples 1 to 3, the amount of the surfactant contained in "deproteinizing agent" was also added.

In accordance with the test procedure described in JIS K 6251, the tensile stress at 500% elongation (500% modulus, $M_{500}$, unit: MPa), the tensile strength $T_B$ (MPa) and the elongation at break $E_B$ (%) were measured.

The thickness of each of the rubber films obtained in the Examples and Comparative Examples was also measured.

The results are shown in Table 2.

TABLE 2

| | | Physical properties of rubber film | | | |
|---|---|---|---|---|---|
| | DPNR Nitrogen, content (N %) | Thickness (mm) | 500% modulus (MPa) | Tensile strength (MPa) | Elongation at break (%) |
| Example 1 | 0.017 | 1.5 | 2.1 | 18.7 | 900 |
| Example 2 | 0.019 | 1.7 | 2.0 | 23.4 | 920 |
| Example 3 | 0.017 | 1.6 | 2.1 | 19.9 | 890 |
| Example 4 | 0.020 | 1.6 | 1.9 | 20.1 | 910 |
| Example 5 | 0.009 | 1.4 | 1.9 | 22.3 | 930 |
| Comp. Example 1 | 0.012 | 0.2 | 1.7 | 23.9 | 910 |
| Comp. Example 2 | 0.013 | 0.2 | 1.9 | 21.5 | 940 |
| Comp. Example 3 | 0.014 | 0.3 | 1.9 | 20.6 | 890 |
| Control* | 0.090 | — | — | — | — |

*In case of "control", no film could be formed.

TABLE 1

| | Deproteinizing agent | | | Number of centrifugation | Amount of |
|---|---|---|---|---|---|
| | Active component | Ratio | Amount | treatment | surfactant |
| Example 1 | Alkaline protease<br>Ammonium polyacryate | 2<br>98 | 1.0 | 1 | 0.3 |
| Example 2 | Alkaline protease<br>Sodium alginate | 2<br>98 | 1.0 | 1 | 0.3 |
| Example 3 | Alkaline protease<br>Sodium polyacrylate | 2<br>98 | 1.0 | 1 | 0.3 |
| Example 4 | Alkaline protease<br>Carboxymethylcellulose | 2<br>98 | 1.0 | 1 | 0.3 |
| Example 5 | Alkaline protease<br>Ammonium polyacrylate | 2<br>98 | 1.0 | 2 | 0.3 |
| Comp. Example 1 | Alkaline protease<br>POE oleyl ether* | 2<br>98 | 1.0 | 1 | (1.28)* |
| Comp. Example 2 | Alkaline protease<br>POE sorbitan monooleate* | 2<br>98 | 1.0 | 1 | (1.28)* |
| Comp. Example 3 | Alkaline protease<br>Sodium rosinate<br>POE nonyl phenyl ether* | 2<br>60<br>38 | 1.0 | 1 | (1.28)* |
| Control | — | — | — | 1 | — |

*"POE" is abbreviation of "polyoxyethylene".

[Evaluation of Characteristics of Natural Rubber Latex]

With respect to the deproteinized natural rubber latexes obtained in Examples and Comparative Examples described above as well as the natural rubber latex after subjected to the blank test, the total nitrogen content (nitrogen content, N %) in the solid content of the latex was determined by the Kjeldahl method.

[Evaluation of Physical Properties of Rubber Film]

Each of the rubber films obtained in the Examples and Comparative Examples was punched to obtain No. 4 dumbbell specimens defined in JIS K 6251 (procedure for tensile test of vulcanized rubber).

As is apparent from the results of Table 1 and Table 2, according to Examples 1 to 5 using the deproteinizing agent composed of a combination of a protease and a water-soluble polymer, it was made possible to obtain a rubber film which has low nitrogen content (capable of realizing high deproteinization) and has a thickness sufficient to use as a work glove and a catheter), and also maintain excellent mechanical strength of the natural rubber itself.

To the contrary, according to Comparative Examples 1 to 3, a rubber film having a sufficient film thickness could not be obtained because of an excess stabilization action caused by the presence of the surfactant.

In case of the control (blank test), since the stability of the latex was drastically lowered by the deproteinization treatment, sufficient film formation could not be conducted.

[Production of Thin Film Dipped Product by Direct Method]

Example 6

(1) Preparation of Deproteinized Natural Rubber Latex

A high ammonia latex of a natural rubber [rubber solid content: 60.0% by weight, pH 11.2, nitrogen content (N %): 0.33%] was diluted so that the rubber solid content of becomes 30% by weight.

An alkaline protease and ammonium polyacrylate as the water-soluble polymer were mixed in a weight ratio of 2:98 and the resulting mixture (deproteinizing agent) was added in the amount of 1 part by weight based on 100 parts by weight of the rubber solid content of the latex and then allowed to stand at 30° C. for 24 hours.

After standing, the latex was subjected to a centrifugation treatment at 13,000 rpm for 30 minutes and the cream component separated in the upper layer was taken out and then dispersed again in water having the same volume as that of the cream component to obtain a deproteinized natural rubber latex.

The nitrogen content (N %) of the deproteinized natural rubber latex thus obtained was measured by the Kjeldahl method. As a result, it was 0.017%.

(2) Preparation of Compound Latex

Based on 100 parts by weight of the rubber solid content of the deproteinized natural rubber latex, 0.8 parts by weight of colloidal sulfur (vulcanizing agent) dispersed in water, 0.5 parts by weight of zinc white (auxiliary vulcanization accelerator) and 0.5 parts by weight of a vulcanization accelerator BZ (zinc dibutyldithiocarbamate, "NOCCELAR BZ" manufactured by Ouchishinko Chemical Industrial Co., Ltd.) were added, followed by maturing (prevulcanization) at 40° C. for 24 hours. After maturing, the compound latex was cooled to 25° C.

(3) Production of Rubber Film

A ceramic test tube (having a diameter of 5 cm) preheated to 50° C. was dipped in the resulting compound latex for heat-sensitive molding for five seconds. A mold was pulled up at a rate of 800 mm/min., and then the rubber film formed on the surface of the mold was dried.

The mold was preheated again to 50° C., dipped in the compound latex for five minutes, and then pulled up at a rate of 1500 mm/min.

After pulling up, the rubber film on the surface of the mold was vulcanized at 100° C. for 30 minutes to obtain a rubber film having a film thickness of 0.10 mm.

Examples 7 to 9

In the same manner as in "(1) preparation of deproteinized rubber latex" of Example 6, except that the following combinations were used as the deproteinizing agent in place of the combination of the alkaline protease and ammonium polyacrylate, deproteinized natural rubber latexes were obtained. The used deproteinizing agents and nitrogen content of the resulting deproteinized natural rubber latexes are shown below.

Example 7: alkaline protease and sodium alginate (weight ratio: 2:98) [nitrogen content (N %): 0.019]

Example 8: alkaline protease and sodium polyacrylate (weight ratio: 2:98) [nitrogen content (N %): 0.017]

Example 9: alkaline protease and carboxymethylcellulose (weight ratio: 2:98) [nitrogen content (N %): 0.020]

In the same manner as in Example 1, except that the resulting deproteinized natural rubber latexes were used, "(2) preparation of compound latex" and "(3) production of rubber film" were conducted.

Example 10

(1) Preparation of Deproteinized Natural Rubber Latex

Using a high ammonia latex of a natural rubber [rubber solid content: 60.0%by weight, pH 11.2, nitrogen content (N %): 0.33%], the dilution, addition of the deproteinizing agent, standing, centrifugation treatment and redispersion were conducted in the same manner as in Example 6.

The latex obtained by the redispersion was subjected to a centrifugation treatment (cleaning treatment) again at 13,000 rpm for 30 minutes.

After the second centrifugation treatment (cleaning treatment), the cream component separated in the upper layer was taken-out and dispersed again in water having the same volume as that of the cream component to obtain a deproteinized natural rubber latex. The nitrogen content of the resulting deproteinized natural rubber latex was measured by the Kjeldahl method. As a result, it was 0.009%.

In the same manner as in Example 6, except that the deproteinized natural rubber latex thus obtained was used, "(2) preparation of compound latex" and "(3) production of rubber films" were conducted to obtain a rubber film.

Comparative Example 4

(1) Preparation of Deproteinized Natural Rubber Latex

A high ammonia latex of a natural rubber [rubber solid content: 60.0% by weight, pH 11.2, nitrogen content (N %): 0.33%] was diluted so that the rubber solid content of becomes 30% by weight.

An alkaline protease and a polyoxyethylene oleyl ester [POE oleyl ester, manufactured from Kao Corp. under the trade name of "EMULGEN 420"] as the nonionic surfactant were mixed in a weight ratio of 2:98 and the resulting mixture (deproteinizing agent) was added in the amount of 1 part by weight based on 100 parts by weight of the rubber solid content of the latex and then allowed to stand at 30° C. for 24 hours.

After standing, the latex was subjected to a centrifugation treatment at 13,000 rpm for 30 minutes and the cream component separated in the upper layer was taken out and then dispersed again in water having the same volume as that of the cream component to obtain a deproteinized natural rubber latex. The nitrogen content of the resulting deproteinized natural rubber latex was measured by the Kjeldahl method. As a result, it was 0.012%.

In the same manner as in Example 6, except that the deproteinized natural rubber latex thus obtained was used, "(2) preparation of compound latex" and "(3) production of rubber film" were conducted to obtain a rubber film.

Comparative Examples 5 and 6

In the same manner as in"(1) preparation of deproteinized rubber latex" of Comparative Example 4, except that the following combinations were used as the deproteinizing agent in place of the combination of the alkaline protease and ammonium polyacrylate, deproteinized natural rubber latexes were obtained. The used deproteinizing agents and nitrogen content of the resulting deproteinized natural rubber latexes are shown below.

Comparative Example 5: alkaline protease and polyoxyethylene sorbitan oleyl ester [POE sorbitan oleyl ester, manufactured from Kao Corp. under the trade name of "RHEODOL TW-O120"] (weight ratio: 2:98) [nitrogen content (N %): 0.013]

Comparative Example 6: alkaline protease, sodium rosinate and polyoxyethylene nonyl phenyl ether[POE nonyl phenyl ether, manufactured from Kao Corp. under the trade name of "EMULGEN 920"] (weight ratio: 2:60:38) [nitrogen content (N %): 0.014]

In the same manner as in Comparative Example 4, except that the resulting deproteinized natural rubber latex was used, "(2) preparation of compound latex" and "(3) production of rubber film" were conducted to obtain a rubber film.

The proteinizing agents and amount thereof, the number of the centrifugation treatment (number of cleaning) and the nitrogen content (N %) of the resulting deproteinized natural rubber latex in "(1) preparation of deproteinized natural rubber latex" of Examples 6 to 10 and Comparative Examples 4 to 6 are shown in Table 3.

The results are shown in Table 4.

TABLE 4

|  | Pull-up rate 800 mm/min. | | | Pull-up rate 1500 mm/min. | | |
| --- | --- | --- | --- | --- | --- | --- |
|  | Film thickness (mm) | Liquid dripping | Uniformity of film | Film thickness (mm) | Liquid dripping | Uniformity of film |
| Example 6 | 0.08 | A | A | 0.10 | A | A |
| Example 7 | 0.10 | A | A | 0.11 | A | A |
| Example 8 | 0.09 | A | A | 0.10 | A | A |
| Example 9 | 0.09 | A | A | 0.11 | A | A |
| Example 10 | 0.08 | A | A | 0.11 | A | A |
| Comp. Example 4 | 0.07 | B | C | 0.08 | C | C |
| Comp. Example 5 | 0.06 | B | C | 0.08 | C | C |
| Comp. Example 6 | 0.06 | B | C | 0.08 | C | C |

As is apparent from Table 4, in case of Examples 6 to 10 wherein the deproteinization treatment was conducted by

TABLE 3

|  | Deproteinizing agent | | Amount of deproteinizing agent*1 | Number of cleaning | Nitrogen content (N %) |
| --- | --- | --- | --- | --- | --- |
|  | Component | Weight ratio | | | |
| Example 6 | Alkaline protease | 2 | 1 part by weight | 1 | 0.017 |
|  | Ammonium polyacryate | 98 | | | |
| Example 7 | Alkaline protease | 2 | 1 part by weight | 1 | 0.019 |
|  | Sodium alginate | 98 | | | |
| Example 8 | Alkaline protease | 2 | 1 part by weight | 1 | 0.017 |
|  | Sodium polyacrylate | 98 | | | |
| Example 9 | Alkaline protease | 2 | 1 part by weight | 1 | 0.020 |
|  | Carboxymethylcellulose | 98 | | | |
| Example 10 | Alkaline protease | 2 | 1 part by weight | 2 | 0.009 |
|  | Ammonium polyacrylate | 98 | | | |
| Comp. Example 4 | Alkaline protease | 2 | 1 part by weight | 1 | 0.012 |
|  | POE oleyl ether | 98 | | | |
| Comp. Example 5 | Alkaline protease | 2 | 1 part by weight | 1 | 0.013 |
|  | POE sorbitan oleyl ether | 98 | | | |
| Comp. Example 6 | Alkaline protease | 2 | 1 part by weight | 1 | 0.014 |
|  | Sodium rosinate | 60 | | | |
|  | POE nonyl phenyl ether | 38 | | | |

*1: The amount of the deproteinizing agent is an amount based on 100 parts by weight of the rubber content of the latex.
*2: "POE" is abbreviation of "polyoxyethylene".

In "(3) production of rubber film" of Examples 6 to 10 and Comparative Examples 4 to 6, the measurement of the film thickness (mm) of the rubber film formed on the surface of the mold and visual evaluation of the presence or absence of liquid dripping as well as uniformity of the film were conducted.

Evaluation criteria for the presence or absence of liquid dripping are as follows.
A: Any liquid dripping was not observed.
B: Slight liquid dripping occurred.
C: Severe liquid dripping occurred.

Evaluation criteria for the uniformity of the film are as follows.
A: The thickness of the film was almost uniform.
B: Although the thickness of the film slightly varied, the variation does not cause any problem in practical use.
C: Variation in thickness of the film was severe enough to be observed easily.

using the deproteinizing agent composed of the protease and the water-soluble polymer, it was made possible to form a rubber film, which has a very small film thickness and is uniform, by the direct (dipping) method.

To the contrary, in case of Comparative Examples 4 to 6 wherein the deproteinization treatment was conducted by using a conventional deproteinizing agent composed of the protease and the surfactant, there arose problems such as liquid dripping and severe uneven film.

[Production of Thick Film Dipped Product by Heat Sensitizing Method]

Example 11

(1) Preparation of Deproteinized Natural Rubber Latex

In the same manner as in "preparation of deproteinized natural rubber latex" in Example 6, a deproteinized natural rubber latex [nitrogen content (N %): 0.017%] was obtained.

(2) Preparation of Heat-sensitive Compound Latex

Based on 100 parts by weight of the rubber solid content of the deproteinized natural rubber latex, 1 part by weight of colloidal sulfur (vulcanizing agent) dispersed in water, 1 part by weight of zinc white (auxiliary vulcanization accelerator), 1 part by weight of a vulcanization accelerator BZ (aforementioned "NOCCELAR BZ") and 0.3 parts by weight of an aromatic glycol ether as the stabilizer were added, followed by maturing (prevulcanization) at 40° C. for 24 hours.

After maturing (prevulcanization), the compound latex was cooled to 25° C. and the pH was adjusted to 8.5 using 10% formalin. Then, polyvinyl methyl ether as the heat sensitizer was added in the amount of 0.5 parts by weight based on 100 parts by weight of the rubber solid content in the latex.

(3) Production of Rubber Film

A ceramic test tube (having a diameter of 5 cm) preheated to 90° C. was dipped in the heat-sensitive compound latex thus obtained for 30 seconds. A mold was pulled up, and then a rubber film having a film thickness of 1.5 mm was obtained by vulcanizing at 100° C. for 90 minutes.

Examples 12 and 13

In the same manner as in Example 11, except that the amount of the heat sensitizer was changed to 0.1 parts by weight (Example 12) or 5.0 parts by weight (Example 13) based on 100 parts by weight of the rubber solid content, preparation of heat-sensitive compound latexes and production of rubber films were conducted.

Examples 14 and 15

In the same manner as in Example 11, except that the amount of the heat sensitizer was changed to 0.05 parts by weight (Example 14) or 12 parts by weight (Example 15) based on 100 parts by weight of the rubber solid content, preparation of heat-sensitive compound latexes and production of rubber films were conducted.

Example 16

In the same manner as in Example 11, except that the deproteinized natural rubber latex is not subjected to the maturing (prevulcanization) treatment, preparation of a heat-sensitive compound latex and production of a rubber film were conducted.

Comparative Example 7

(1) Preparation of Deproteinized Natural Rubber Latex

A high ammonia latex of a natural rubber [rubber solid content: 60.0% by weight, pH 11.2, nitrogen content (N %): 0.33%] was diluted so that the rubber solid content of becomes 30% by weight.

An alkaline protease, sodium laurate as the anionic surfactant and "EMULGEN 810" [manufactured, from Kao Corp., polyoxyethylene octyl phenyl ether] as the nonionic surfactant were mixed in a weight ratio of 2:60:38and the resulting mixture (deproteinizing agent) was added in the amount of 1 part by weight based on 100 parts by weight of the rubber solid content of the latex and then allowed to stand at 30° C. for 24 hours.

After standing, the latex was subjected to a centrifugation treatment at 13,000 rpm for 30 minutes and the cream component separated in the upper layer was taken out and then dispersed again in water having the same volume as that of the cream component to obtain a deproteinized natural rubber latex.

The nitrogen content of the resulting deproteinized natural rubber latex was measured by the Kjeldahl method. As a result, it was 0.011%.

(2) Preparation of Heat-sensitive Compound Latex and (3) Production of Rubber Film In the same manner as in Example 11, except that the above latex (obtained by subjecting to a deproteinization treatment in the presence of a protease, an anionic surfactant and a nonionic surfactant) was used as the deproteinized natural rubber latex in place of the latex obtained by subjecting to a deproteinization treatment in the presence of a protease and a water-soluble polymer (Example 11), preparation of a heat-sensitive compound latex and production of a rubber film were conducted.

Comparative Example 8

In the same manner as in Comparative Example 7, except that the amount of the heat sensitizer was changed to 5.0 parts by weight based on 100 parts by weight of the rubber solid content, preparation of a compound latex having the heat sensitivity and production of a rubber film were conducted.

Comparative Example 9

A high ammonia (HA) latex used in the preparation of the deproteinized natural rubber latex was diluted so that the rubber solid content of becomes 30% by weight.

In the same manner as in Comparative Example 11, except that the diluted HA latex described above was used in place of the deproteinized natural rubber latex, preparation of a heat-sensitive compound latex and production of a rubber film were conducted.

[Evaluation of Physical Properties of Rubber Film]

With respect to the rubber films obtained in Examples, 11 to 16 and Comparative Examples 7 to 9, the thickness, the tensile stress $T_B$, the elongation at break $E_B$ and the modulus $M_{500}$ were measured and, moreover, the evaluation of the film forming properties was also conducted in the formation of the rubber film. The procedure for measurement and evaluation is as follows.

Thickness of Rubber Film

The thickness of the resulting rubber film was measured at three points in total and an average value thereof was taken as the thickness.

Evaluation of Film Forming Properties

The variation in thickness of the resulting rubber film was visually observed and evaluated according to the following criteria.

AA: The uniformity of the thickness of the film was remarkably high.

A: The thickness of the film was almost uniform.

B: Although the thickness of the film slightly varied, the variation does not cause any problem in practical use.

C: Variation in thickness of the film was severe enough to be observed easily, and occurrence of liquid dripping was also observed.

Measurement of tensile stress $T_B$, elongation at break $E_B$ and modulus $M_{500}$ Specimens for tensile test (No. 3 dumbbell-shape) defined in JIS K 6301 were made and used as samples.

In accordance with "tensile test" defined in JIS K 6301, the thickness, the tensile stress $T_B$ (MPa), the elongation at break $E_B$ (%) and the modulus (tensile stress) $M_{500}$ (MPa) were measured.

The results are shown in Table 5.

TABLE 5

| | Latex | | | Evaluation of physical properties | | | | |
|---|---|---|---|---|---|---|---|---|
| | Stabilizing agent*1 | Amount of heat sensitizer*2 | Presence or absence of prevulcanization | Thickness*3 of rubber film | Film forming properties | Tensile strength $T_B$*4 | Elongation at break $E_B$*5 | Modulus $M_{500}$*6 |
| Example 11 | WP | 0.5 | Yes | 1.5 | AA | 18.7 | 900 | 2.1 |
| Example 12 | WP | 0.1 | Yes | 0.4 | A | 21.6 | 930 | 1.8 |
| Example 13 | WP | 5.0 | Yes | 2.9 | A | 20.3 | 910 | 2.0 |
| Example 14 | WP | 0.05 | Yes | 0.2 | B | 20.9 | 920 | 1.8 |
| Example 15 | WP | 12 | Yes | 4.3 | B | 18.9 | 900 | 2.1 |
| Example 16 | WP | 0.5 | No | 1.4 | AA | 16.9 | 940 | 1.6 |
| Comp. Example 7 | SA | 0.5 | Yes | 0.2 | C | 23.9 | 910 | 1.7 |
| Comp. Example 8 | SA | 5.0 | Yes | 0.2 | C | 21.5 | 940 | 1.9 |
| Comp. Example 9 | — | 0.5 | Yes | 1.6 | AA | 22.4 | 840 | 2.9 |

*1: It is a stabilizer added during the deproteinization treatment, while WP represents a water-soluble polymer and SA represents a surfactant.
*2: It represents an amount (parts by weight) based on 100 parts by weight of the rubber solid content of the deproteinized natural rubber latex.
*3: Its unit is [mm]
*4, 6: Its unit is [MPa].
*5: Its unit is [%].

As is apparent from the results of Table 5, according to Examples 11 to 16, it was made possible to produce rubber films which show good film forming properties while maintaining excellent mechanical properties of the natural rubber itself. In Examples 11 to 14, the film forming properties were very good. The latexes of Examples 11 to 16 were also superior in stability.

Accordingly, according to the present invention, it is made possible to obtain a dipped product having a sufficient film thickness, which can easily control heat sensitizing characteristics by using a highly deproteinized natural rubber latex as a raw material in accordance with the same formulation as that of a conventional heat-sensitive latex using a natural rubber latex.

As shown in Comparative Examples 7 and 8, according to a conventional method using a surfactant as a stabilizer during the deproteinization treatment, only a very thin film can be formed and the film forming properties are very poor.

In case of Comparative Example 9 using a conventional non-deproteinized high ammonia latex as the rubber latex, the heat sensitizing properties and film forming properties are sufficient, but allergy caused by the protein can not be eliminated.

The disclosures of Japanese Patent Application Nos. 2000-130543, 2000-140535 and 2000-248902, filed on Apr. 28, 2000, May 12, 2000 and Aug. 18, 2000, respectively, are incorporated herein by reference.

What is claimed is:

1. A method of producing a rubber product, which comprises adding a protease and one or more water-soluble polymers to a natural rubber latex, thereby subjecting the natural rubber latex to a deproteinization treatment, incorporating at least a vulcanizing agent into the latex, dipping a mold in the resulting compound latex, and vulcanizing and drying a rubber film formed on the mold, wherein said one or more water-soluble polymers have at least one hydrophilic functional group selected from the group consisting of a hydroxyl group, a carboxyl group, an amide group, an ester bond, and salts thereof, with a principal chain of (meth) acrylate polymer, alginate polymer, vinyl polymer, or cellulose polymer having from 100 to 5,000,000 carbon atoms.

2. A method of producing a rubber product, which comprises adding a protease and one or more water-soluble polymers to a natural rubber latex, thereby subjecting the natural rubber latex to a deproteinization treatment, incorporating at least a heat sensitizer and a vulcanizing agent into the latex, dipping a mold in the resulting heat-sensitive coagulable compound latex, and vulcanizing and drying a rubber film formed on the mold, wherein said one or more water-soluble polymers have at least one hydrophilic functional group selected from the group consisting of a hydroxyl group, a carboxyl group, an amide group, an ester bond, and salts thereof, with a principal chain of (meth) acrylate polymer, alginate polymer, vinyl polymer, or cellulose polymer having from 100 to 5,000,000 carbon atoms.

3. The method of producing a rubber product according to claim 2, wherein the heat sensitizer is a water-soluble polymer type heat sensitizer.

4. The method of producing a rubber product according to claim 2, wherein the amount of the heat sensitizer is within a range from 0.1 to 10 parts by weight based on 100 parts by weight of the rubber solid content in the deproteinized latex.

5. The method of producing a rubber product according to claim 3, wherein the amount of the heat sensitizer is within a range from 0.1 to 10 parts by weight based on 100 parts by weight of the rubber solid content in the deproteinized latex.

* * * * *